US012392085B2

(12) United States Patent
Magurudeniya et al.

(10) Patent No.: US 12,392,085 B2
(45) Date of Patent: Aug. 19, 2025

(54) USE OF IN-SITU IONIC LIQUID (IL) AND DEEP EUTECTIC SOLVENT (DES) SYNTHESIS USING CHEMICALLY SYNTHESIZED OR BIOMASS-DERIVED IONS IN THE PRETREATMENT OF BIOMASS

(71) Applicants: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US)

(72) Inventors: Harsha D. Magurudeniya, Newport News, VA (US); Ezinne Achinivu, Alexandria, VA (US); Blake A. Simmons, San Francisco, CA (US); John M. Gladden, Alameda, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

(*) Notice: Subject to any disclaimer, the term of this patent is extended or adjusted under 35 U.S.C. 154(b) by 403 days.

(21) Appl. No.: 17/339,909

(22) Filed: Jun. 4, 2021

(65) Prior Publication Data
US 2021/0363696 A1   Nov. 25, 2021

Related U.S. Application Data (63) Continuation-in-part of application No. 17/242,256, filed on Apr. 27, 2021.

(60) Provisional application No. 63/035,508, filed on Jun. 5, 2020, provisional application No. 63/016,877, filed on Apr. 28, 2020.

(51) Int. Cl.
*D21C 3/20* (2006.01)
*C12P 19/02* (2006.01)
*C12P 19/14* (2006.01)

(52) U.S. Cl.
CPC ............ *D21C 3/20* (2013.01); *C12P 19/02* (2013.01); *C12P 19/14* (2013.01); *C12P 2201/00* (2013.01)

(58) Field of Classification Search
CPC ... D21C 3/20; D21C 1/04; D21C 3/04; D21C 3/222; D21C 5/005; C12P 19/02; C12P 19/14; C12P 2201/00; Y02P 20/54
See application file for complete search history.

(56) References Cited

U.S. PATENT DOCUMENTS

| | | |
|---|---|---|
| 6,177,575 B1 | 1/2001 | Arduengo, III et al. |
| 7,985,567 B2 | 7/2011 | Chou et al. |
| 8,420,833 B2 | 4/2013 | Katz et al. |
| 8,852,902 B2 | 10/2014 | Katz et al. |
| 9,109,175 B2 | 8/2015 | Lee et al. |
| 9,200,298 B2 | 12/2015 | Lee et al. |
| 9,322,042 B2 | 4/2016 | Sapra et al. |
| 9,334,514 B2 | 5/2016 | Fortman et al. |
| 9,376,691 B2 | 6/2016 | Peralta-Yahya et al. |
| 9,376,728 B2 | 6/2016 | Zhang et al. |
| 9,382,553 B2 | 7/2016 | Kirby et al. |
| 9,624,482 B2 | 4/2017 | Sapra et al. |
| 9,631,210 B2 | 4/2017 | Chou et al. |
| 9,725,749 B2 | 8/2017 | Chen et al. |
| 9,765,044 B2 | 9/2017 | Socha et al. |
| 9,803,182 B2 | 10/2017 | Gladden et al. |
| 9,862,982 B2 | 1/2018 | Zhang et al. |
| 9,951,345 B2 | 4/2018 | Steen et al. |
| 10,155,735 B2 | 12/2018 | Socha et al. |
| 10,167,488 B2 | 1/2019 | Keasling et al. |
| 2004/0097755 A1 | 5/2004 | Abbott et al. |
| 2010/0196967 A1 | 8/2010 | Edye et al. |

(Continued)

FOREIGN PATENT DOCUMENTS

| | | |
|---|---|---|
| WO | 2009/006386 A2 | 1/2009 |
| WO | 2009/006429 A1 | 1/2009 |

(Continued)

OTHER PUBLICATIONS

Sunol, et al. "Definition and Composition of Deep Eutectic Solvents", 2019, Handbook of Solvents, Third Edition. (Year: 2019).*
Yu, Qiang; et al. "In situ deep eutectic solvent pretreatment to improve lignin removal from garden wastes and enhance production of bio-methane and microbial lipid", 2019, Bioresource Technology, 271, 210-217. (Year: 2019).*
Yu, Qiang; et al. "In situ deep eutectic solvent pretreatment to improve lignin removal from garden wastes and enhance production of bio-methane and microbial lipids", 2019, Bioresource Technology, 271, 210-217. (Year: 2019).*
Chen et al. "Distillable Ionic Liquids: reversible Amide O Alkylation", Angewandte Comm. 52:13392-13396 (2013).

(Continued)

*Primary Examiner* — Kade Ariani
(74) *Attorney, Agent, or Firm* — Robin C. Chiang; LAWRENCE BERKELEY NATIONAL LABORATORY (57) ABSTRACT

The present invention provides for a method to deconstruct a biomass comprising: (a) introducing one or more individual components of an ionic liquid (IL) or deep eutectic solvent (DES) to a biomass, wherein the one or more individual components, and optionally any components already present in the biomass, form an IL or DES, or mixture thereof, which solubilizes the biomass to form a solubilized biomass mixture, wherein at least one individual component is introduced to the biomass separately from any other individual component; (b) optionally introducing an enzyme and/or a microbe to the solubilized biomass mixture such that the enzyme and/or microbe produces a sugar from the solubilized biomass mixture; and, (c) optionally separating the sugar from the solubilized biomass mixture.

17 Claims, 3 Drawing Sheets

(56) References Cited

U.S. PATENT DOCUMENTS

| | | | | |
|---|---|---|---|---|
| 2011/0318803 A1* | 12/2011 | Hitz | .................. | C12P 7/065 |
| | | | | 435/162 |
| 2014/0178944 A1* | 6/2014 | Parekh | .................. | A23K 30/15 |
| | | | | 435/99 |
| 2018/0305656 A1* | 10/2018 | Wendt | .................. | C12N 1/04 |
| 2019/0203012 A1* | 7/2019 | Shi | .................. | C08J 11/16 |
| 2020/0216863 A1 | 7/2020 | Xu et al. | | |

FOREIGN PATENT DOCUMENTS

| | | | | |
|---|---|---|---|---|
| WO | 2009/006430 A1 | 1/2009 | | |
| WO | 2009/134899 A2 | 5/2009 | | |
| WO | 2010/127318 A2 | 4/2010 | | |
| WO | WO-2010073083 A2 * | 7/2010 | .............. | C12P 19/14 |
| WO | 2010124266 A2 | 10/2010 | | |
| WO | 2012/050931 A2 | 4/2012 | | |
| WO | 2012/135389 A2 | 4/2012 | | |
| WO | 2012/058686 A2 | 5/2012 | | |
| WO | 2012/064740 A1 | 5/2012 | | |
| WO | 2012/071439 A1 | 5/2012 | | |
| WO | 2012151214 A1 | 11/2012 | | |
| WO | 2014/093402 A2 | 6/2014 | | |
| WO | 2015013674 A2 | 1/2015 | | |
| WO | 2016/070125 A1 | 5/2015 | | |
| WO | 2016105538 A1 | 6/2016 | | |
| WO | 2017087982 A1 | 5/2017 | | |
| WO | 2017091781 A1 | 6/2017 | | |
| WO | 2017214159 A1 | 12/2017 | | |
| WO | 2017214332 A1 | 12/2017 | | |
| WO | 2018119152 A1 | 6/2018 | | |
| WO | 2018/200888 A1 | 11/2018 | | |
| WO | 2018204424 A1 | 11/2018 | | |
| WO | 2019050990 A1 | 3/2019 | | |

OTHER PUBLICATIONS

King et al. "Distillable Acid-Base Conjugate Ionic Liquids for Cellulose Dissolution and Processing", Angewandte Comm. 50:6301-6305 (2011).

Vijayaraghavan et al. "CO2-based Alkyl Carbamate Ionic Liquids as Distillable Extraction Solvents", ACS Sustainable Chem. Engin. 2:31724-1728 (2014).

Idris et al. "Distillable Protic Ionic Liquids for Keratin Dissolution and Recovery", ACS Sustainable Chem. Engin. 2:1888-1894 (2014).

Sun et al. "One-pot integrated biofuel production using low-cost biocompatible protic ionic liquids", Green Chem. 19 (13):3152-3163 (2017).

Greaves et al. "Protic Ionic Liquids: Properties and Applications" Chem. Rev. 108(1):206-237 (2008).

* cited by examiner

USE OF IN-SITU IONIC LIQUID (IL) AND DEEP EUTECTIC SOLVENT (DES) SYNTHESIS USING CHEMICALLY SYNTHESIZED OR BIOMASS-DERIVED IONS IN THE PRETREATMENT OF BIOMASS

CROSS-REFERENCE TO RELATED APPLICATIONS

This application claims priority to U.S. Provisional Patent Application Ser. No. 63/035,508, filed on Jun. 5, 2020, and claims priority as a continuation-in-part application of U.S. patent application Ser. No. 17/242,256, filed on Apr. 27, 2021, which in turn claims priority to U.S. Provisional Patent Application Ser. No. 63/016,877, filed on Apr. 28, 2020, which are all hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of biomass pretreatment.

BACKGROUND OF THE INVENTION

Pretreatment of lignocellulosic biomass is an essential step in any lignocellulosic conversion technology. Current pretreatment methods based on severe physio-chemical processes are effective, but they can be costly and energy intensive. Alternatively, many ionic liquids (ILs) and deep eutectic solvents (DES) have been shown to be effective at biomass pretreatment and require less severe pretreatment conditions to reduce the recalcitrance of lignocellulose to enzymatic hydrolysis. For example, cholinium lysinate in 90% water, has been demonstrated to be effective for biomass pretreatment in a one-pot configuration owing to its effectiveness in solubilizing lignin. However, ILs/DESs contribute to the overall cost of a lignocellulosic conversion process, so methods to reduce their costs can have a big impact on the overall economics of a biorefinery. Therefore, this invention features a way to synthesize the IL/DES in-situ (during pretreatment), by the direct addition of one or more of the reagents along with the biomass into the pretreatment vessel.

Ionic liquids (ILs) and deep eutectic solvents (DES) have been shown to be effective solvents for pretreatment of lignocellulose, reducing its recalcitrance to enzymatic hydrolysis. However, ionic liquids and deep eutectic solvents can be expensive and therefore methods that reduce IL/DES use or cost, will reduce overall costs within a biorefinery.

SUMMARY OF THE INVENTION

The present invention provides for a method to deconstruct a biomass: the method comprising: (a) introducing one or more individual components of an ionic liquid (IL) or deep eutectic solvent (DES) to a biomass, wherein the one or more individual components, and optionally any components already present in the biomass, form an ionic liquid (IL) or deep eutectic solvent (DES), or mixture thereof, which solubilizes the biomass to form a solubilized biomass mixture, wherein at least one individual component is introduced to the biomass separately from any other individual component; (b) optionally introducing an enzyme and/or a microbe to the solubilized biomass mixture such that the enzyme and/or microbe produces a sugar from the solubilized biomass mixture; and, (c) optionally separating the sugar from the solubilized biomass mixture.

In some embodiments, the one or more individual components are selected from the group consisting of molecules that can form ILs: cations (such as an amine containing molecules such as ethanolamine, choline, and the like) and anions (such as mineral and organic acids, such as sulfuric acid, acetic acid, and the like). In some embodiments, the introducing step (a) comprises introducing two or individual components to the biomass, wherein the two or individual components form an IL, or mixture thereof. In some embodiments, the components already present in the biomass are components that are naturally found in a biomass.

In some embodiments, the one or more individual components are selected from the group consisting of molecules that can form DES, such as halide and organic salts (such as choline chloride, zinc chloride, ammonium acetate, and the like), organic acids (such as acetic, lactic, tartaric, etc.), polyols (such as ethylene glycol, propanediol, glycerol, glucose, etc.), amines (such as urea, acetamine, thiourea, and the like).

In some embodiments, the introducing step (a) comprises introducing two or individual components to the biomass, wherein the two or individual components form a DES, or mixture thereof.

In some embodiments, the introducing step (a) comprises introducing each individual component separately to the biomass.

In some embodiments, the method further comprises ensiling a biomass, prior to the introducing step (a), to produce an ensiled biomass comprising one or more organic acids, wherein the ensile biomass is the biomass of the introducing step (a). In some embodiments, the ensiled biomass comprises equal to or more than about 10%, 20%, 30%, or 40% by weight of the one or more organic acids. In some embodiments, the one or more organic acids comprises an alkanoic acid. In some embodiments, the alkanoic acid is lactic acid, acetic acid, butyric acid, or propionic cid, or a mixture thereof.

In some embodiments, the method further comprises one or more steps taught in U.S. Provisional Patent Application Ser. No. 63/016,877, filed Apr. 28, 2020, and U.S. patent application Ser. No. 17/242,256, filed Apr. 27, 2021 (both are hereby incorporated by reference in their entireties). In some embodiments, the method further comprises: ensiling a biomass to produce one or more organic acids, and/or introducing a solvent to the ensiled biomass to dissolve at least part of solid biomass in the solvent, wherein the solvent is an ionic liquid (IL) or deep eutectic solvent (DES), or mixture thereof, prior to step (a). In some embodiments, the introducing step (a) comprises: (i) ensiling a biomass to produce one or more organic acids, and (ii) introducing a solvent to the ensiled biomass to dissolve at least part of solid biomass in the solvent, wherein the solvent is an ionic liquid (IL) or deep eutectic solvent (DES), or mixture thereof, to form a solubilized biomass mixture.

In some embodiments, the one or more individual components comprise choline hydroxide or choline chloride.

In some embodiments, the method further comprises (b) introducing an enzyme and/or a microbe to the solubilized biomass mixture such that the enzyme and/or microbe produces a sugar from the solubilized biomass mixture.

In some embodiments, the method further comprises (c) separating the sugar from the solubilized biomass mixture.

In some embodiments, the method results in a yield of equal to or more than about 80%, 85%, 90%, or 95% of sugar from the biomass.

In some embodiments, step (a) does not comprise, or lacks, introducing or adding any water to the biomass or mixture. In some embodiments, the amount of water in the mixture, excluding or including water or moisture naturally found in the biomass is no more than about 10%, 9%, 8%, 7%, 6%, 5%, 4%, 3%, 2%, 1%, 0.5%, or 0.1% by weight or volume of the mixture.

The present invention provides for compositions and methods described herein. In some embodiments, the compositions and methods further comprise steps, features, and/or elements described in U.S. patent application Ser. No. 16/737,724, hereby incorporated by reference in its entirety.

In some embodiments, the method, or one-pot method, does not require any solid-liquid separation step. In some embodiments, the one-pot method does not require adjustment of the pH level in the one-pot composition. In some embodiments, the one-pot method does not require any dilution, or addition of water or medium, after pretreatment and/or before saccharification and fermentation. In some embodiments, the reaction of the enzyme and the growth of the microbe occur in the same one-pot composition. In some embodiments, the IL, DES, or mixture thereof, is renewable as it can be continuous in use. In some embodiments, the one-pot method can produce a yield of sugar that is equal to or more than about 50%, 60%, 70%, 75%, or 80%, or any other value described herein.

In some embodiments, using bio-compatible solvents enables a one-pot biomass conversion which eliminates the needs of mass transfer between reactors and the separation of solid and liquid. In some embodiments, the method does not require recycling any catalyst and/or enzyme. In some embodiments, the method requires less water usage than current biomass pretreatment. The method can produce fuels/chemicals at a higher titer and/or yield in a single vessel without any need for intermediate units of mass transfer and/or solid/liquid separation.

In some embodiments, the ensiling step produces one or more toxic compounds in the ensiled biomass, and the microbe is resistant to the one or more toxic compounds.

In some embodiments, the one or more toxic compound is an organic acid, such as a straight chained or branched alkanoic acid (such as acetic acid, lactic acid, or formic acid), or an aromatic organic acid (such as benzoic acid, vanillic acid, or the like). In some embodiments, the organic acid has between about 2 to 10 carbon atoms.

The present invention provides for compositions and methods described herein.

In some embodiments, the compositions and methods further comprise steps, features, and/or elements described in U.S. patent application Ser. No. 16/737,724, hereby incorporated by reference in its entirety.

The present invention provides for a method to deconstruct a biomass: the method comprising: (a) introducing one or more individual components of an ionic liquid (IL) or deep eutectic solvent (DES) and/or biomass to a one-pot composition, wherein the one or more individual components, and optionally any components already present in the biomass, form an ionic liquid (IL) or deep eutectic solvent (DES) or mixture thereof, which solubilizes the biomass to form a solubilized biomass mixture in the one-pot composition, wherein at least one individual component is introduced to the biomass separately from any other individual component; (b) optionally introducing an enzyme and/or a microbe to the one-pot composition such that the enzyme and/or microbe produces a sugar from the solubilized biomass mixture; (c) optionally separating the sugar from the one-pot composition; wherein the introducing steps (a) and (b), and optionally the separating step (c), are continuous.

In some embodiments, the method, or one-pot method, does not require any solid-liquid separation step. In some embodiments, the one-pot method does not require adjustment of the pH level in the one-pot composition. In some embodiments, the one-pot method does not require any dilution, or addition of water or medium, after pretreatment and/or before saccharification and fermentation. In some embodiments, the reaction of the enzyme and the growth of the microbe occur in the same one-pot composition. In some embodiments, the IL, DES, or mixture thereof, is renewable as it can be continuous in use. In some embodiments, the one-pot method can produce a yield of sugar that is equal to or more than about 50%, 60%, 70%, 75%, or 80%, or any other value described herein.

In some embodiments, using bio-compatible DESs enables a one-pot biomass conversion which eliminates the needs of mass transfer between reactors and the separation of solid and liquid. In some embodiments, the method does not require recycling any catalyst and/or enzyme. In some embodiments, the method requires less water usage than current biomass pretreatment. The method can produce fuels/chemicals at a higher titer and/or yield in a single vessel without any need for intermediate units of mass transfer and/or solid/liquid separation.

The present invention provides for a method for synthesize IL/DESs by directly adding their individual components to the pretreatment reactor along with the lignocellulosic feedstock, then immediately proceeding with pretreatment. In some embodiments, the IL/DES is synthesized within the pretreatment reaction, thus removing the need to synthesize the IL/DES in advance, which is a process with can be costly and time-consuming. In some embodiments, the IL/DES is also synthesized using ions present within the biomass. In some embodiments, the biomass is ensiled biomass. In some embodiments, the ensiled biomass accumulates around about 10-14 wt % of organic acids, such as lactic and acetic acid, that can be used as anions or hydrogen bond donors in ILs and/or DESs, respectively. In some embodiments, choline hydroxide is added to synthesize choline lactate/acetate. In some embodiments, choline chloride is added to synthesize the DES choline chloride lactic/acetic acid.

ILs/DESs are typically synthesized prior to use for biomass pretreatment. However, in the present invention, in some embodiments, the method lacks this step, and the synthesis is combined with biomass pretreatment. In some embodiments, one or more IL/DES components are introduced or added directly to the biomass in the pretreatment reactor, and pretreatment is run as normal, such as in a method previously taught. In some embodiments, the IL ethanolamine acetate ([Eth][OAc]) is synthesized by adding ethanolamine and acetic acid in an about 1:1 molar ratio directly to the biomass in a pretreatment reactor. The resulting biomass (post pretreatment) is just as easily hydrolyzed into fermentable sugars as when using pre-synthesized IL, such as ethanolamine acetate, thereby demonstrating the pretreatment effectiveness did not change. In some embodiments, [Eth][OAc] treated biomass releases about 330 mg/g biomass of sugars during enzymatic hydrolysis, which does not change significantly when the IL is synthesized in-situ or prior to addition to the reactor.

In some embodiments, IL is synthesized using the organic acids present in ensiled biomass. Compositional analysis of dry ensiled *sorghum* biomass confirms that it contains about 10-14 wt % organic acids (such as lactic acid, acetic acid, or the like). These acids are known components of some ionic liquids, therefore they can be used to synthesize ionic liquids "in-situ" by adding the cation in base form to neutralize the acids and form a salt. In some embodiments, the resulting ionic liquid using choline hydroxide is cholinium lactate/acetate. After pretreatment using this in-situ synthesized ionic liquid, enzymatic saccharification of the biomass at 50° C. released about 90% of the maximum theoretical glucose from ensiled *sorghum* at about 20 wt % loading.

The present invention described herein has the one or more of the following key points of differentiation when compared to other methods: (1) Provides a cheap route to synthesizing ILs. (2) Utilizes endogenous organic acids. (3) Results in high sugar conversion efficiencies. (4) Organic acids produced during ensiling can be used as an additional carbon source for bioconversion. (5) Minimizes IL losses due to transfer between vessels. (6) Minimizes impurity formation and the need for IL purification, and the use of solvents during synthesis.

In some embodiments, for the choline based ILs, the water recovered during the synthesis does not need to be dried and is included a part of the pretreatment solvents.

In some embodiments, the biomass acts as a heat sink to absorb any energy released during the IL synthesis, thereby, avoiding the use of organic solvents and minimizing the formation of side products.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" when applied to a value, describes a value that includes up to 10% more than the value described, and up to 10% less than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In some embodiments, the one-pot biomass pretreatment, saccharification, and fermentation is performed using bio-compatible deep eutectic solvents (DESs), or individual components thereof. The used bio-compatible DESs are tested for microbial, such as yeast, compatibility and toxicity. The pretreatment efficacy of the selected DESs are tested. The uses of the DESs for biomass processing eliminates the need to remove any solvent after biomass pretreatment, thus making the one-pot approach possible.

In some embodiments, the introducing step (a) comprises contacting a biomass and one or more individual components of an IL and/or DES. In some embodiments, the contacting step comprises introducing, adding and/or mixing the biomass with the one or more individual components of an IL and/or DES, or vice versa.

In some embodiments, the introducing one or more individual components of an IL and/or DES to a biomass takes place in a vessel and homogenized. In some embodiments, the loading is solid loading and controlled at about 5%, 10%, 15%, 20%, 25%, 30%, 35%, or 40%, or a range within any two preceding values. In some embodiments, the biomass and IL and/or DES components are heated, such as to 100° C., 110° C., 120° C., 130° C., 140° C., 150° C., 160° C., 170° C., 180° C., 190° C., 200° C., 200° C., 212° C., or a range within any two preceding values, for a period of time, such as about 1 h, 2 h, 3 h, 4 h, or 5 h, or a range within any two preceding values. In some embodiments, after pretreatment, the mixture is cooled, such as for a period of about at least 30 mins, such as at room temperature, or about 25° C., and/or then washed at least about 1×, 2×, 3×, 4×, or 5× with water, such as deionized water. In some embodiments, the resulting solid is recovered, such as separating the solid portion with the liquid portion.

In some embodiments, the biomass is a lignocellulosic biomass. In some embodiments, the vessel is made of a material that is inert, such as stainless steel or glass, that does not react or interfere with the reactions in the pretreatment mixture.

In some embodiments, the method uses a one-pot methodology, for example, using method steps and compositions as taught in U.S. patent application Ser. No. 16/737,724 (which is incorporated by reference). In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the method produces a sugar and a lignin from the biomass. The lignin can further be processed to produce a DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the steps (a) and (b), and optionally steps (c) and/or (d), are continuous, the one-pot composition is in a steady state.

Ionic Liquid

Ionic liquids (ILs) are salts that are liquids rather than crystals at room temperatures. It will be readily apparent to those of skill that numerous ILs can be used in the present invention. In some embodiments of the invention, the IL is suitable for pretreatment of the biomass and for the hydrolysis of cellulose by thermostable cellulase. Suitable ILs are taught in ChemFiles (2006) 6(9) (which are commercially available from Sigma-Aldrich, Milwaukee, Wis.). Such suitable ILs include, but are not limited to, 1-alkyl-3-alkylimidazolium alkanate, 1-alkyl-3-alkylimidazolium alkyl sulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

In some embodiments, the IL includes, but is not limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethyl sulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM $AlCl_4$), 1-butyl-3-methylimidazolium thiocyanate (BMIM SCN), 1-ethyl-2,3-dimethylimidazolium ethyl sulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methyl sulfate, tributylmethylammonium methylsulfate, choline acetate, choline salicylate, and the like.

In some embodiments, the ionic liquid is a chloride ionic liquid. In other embodiments, the ionic liquid is an imidazolium salt. In still other embodiments, the ionic liquid is a 1-alkyl-3-imidazolium chloride, such as 1-ethyl-3-methylimidazolium chloride or 1-butyl-3-methylimidazolium chloride.

In some embodiments, the ionic liquids used in the invention are pyridinium salts, pyridazinium salts, pyrimidium salts, pyrazinium salts, imidazolium salts, pyrazolium salts, oxazolium salts, 1,2,3-triazolium salts, 1,2,4-triazolium salts, thiazolium salts, isoquinolium salts, quinolinium salts isoquinolinium salts, piperidinium salts and pyrrolidinium salts. Exemplary anions of the ionic liquid include, but are not limited to halogens (e.g., chloride, floride, bromide and iodide), pseudohalogens (e.g., azide and isocyanate), alkyl carboxylate, sulfonate, acetate and alkyl phosphate.

Additional ILs suitable for use in the present invention are described in U.S. Pat. Nos. 6,177,575; 9,765,044; and, 10,155,735; U.S. Patent Application Publication Nos. 2004/0097755 and 2010/0196967; and, PCT International Patent Application Nos. PCT/US2015/058472, PCT/US2016/063694, PCT/US2017/067737, and PCT/US2017/036438 (all of which are incorporated in their entireties by reference). It will be appreciated by those of skill in the art that others ILs that will be useful in the process of the present invention are currently being developed or will be developed in the future, and the present invention contemplates their future use. The ionic liquid can comprise one or a mixture of the compounds.

In some embodiments, the IL is a protic ionic liquid (PIL). Suitable protic ionic liquids (PILs) include fused salts with a melting point less than 100° C. with salts that have higher melting points referred to as molten salts. Suitable PPILs are disclosed in Greaves et al. "Protic Ionic Liquids: Properties and Applications" Chem. Rev. 108(1):206-237 (2008). PILs can be prepared by the neutralization reaction of certain Brønsted acids and Brønsted bases (generally from primary, secondary or tertiary amines, which are alkaline) and the fundamental feature of these kinds of ILs is that their cations have at least one available proton to form hydrogen bond with anions. In some embodiments, the protic ionic liquids (PILs) are formed from the combination of organic ammonium-based cations and organic carboxylic acid-based anions. PILs are acid-base conjugate ILs that can be synthesized via the direct addition of their acid and base precursors. In some embodiments, the PIL is a hydroxyalkylammonium carboxylate. In some embodiments, the hydroxyalkylammonium comprises a straight or branched C1, C2, C3, C4, C5, C6, C7, C8, C9, or C10 chain. In some embodiments, the carboxylate comprises a straight or branched C1, C2, C3, C4, C5, C6, C7, C8, C9, or C10 chain. In some embodiments, the carboxylate is substituted with one or more hydroxyl groups. In some embodiments, the PIL is a hydroxyethyl ammonium acetate.

In some embodiments, the protic ionic liquid (PIL) is disclosed by U.S. Patent Application Publication No. 2004/0097755, hereby incorporated by reference.

Suitable salts for the method include combinations of organic ammonium-based cations (such as ammonium, hydroxyalkylammonium, or dimethylalkylammonium) with organic carboxylic acid-based anions (such as acetic acid derivatives (C1-C8), lactic acid, glycolic acid, and DESs such as ammonium acetate/lactic acid).

Suitable IL, such as distillable IL, are disclosed in Chen et al. "Distillable Ionic Liquids: reversible Amide O Alkylation", *Angewandte Comm.* 52:13392-13396 (2013), King et al. "Distillable Acid-Base Conjugate Ionic Liquids for Cellulose Dissolution and Processing", *Angewandte Comm.* 50:6301-6305 (2011), and Vijayaraghavan et al. "$CO_2$-based Alkyl Carbamate Ionic Liquids as Distillable Extraction Solvents", *ACS Sustainable Chem. Engin.* 2:31724-1728 (2014), all of which are hereby incorporated by reference.

Suitable PIL, such as distillable PIL, are disclosed in Idris et al. "Distillable Protic Ionic Liquids for Keratin Dissolution and Recovery", *ACS Sustainable Chem. Engin.* 2:1888-1894 (2014) and Sun et al. "One-pot integrated biofuel production using low-cost biocompatible protic ionic liquids", *Green Chem.* 19(13):3152-3163 (2017), all of which are hereby incorporated by reference.

In some embodiments, the PILs are formed with the combination of organic ammonium-based cations and organic carboxylic acid-based anions. PILs are acid-base conjugate ILs that can be synthesized via the direct addition of their acid and base precursors. Additionally, when sufficient energy is employed, they can dissociate back into their neutral acid and base precursors, while the PILs are re-formed upon cooling. This presents a suitable way to recover and recycle the ILs after their application. In some embodiments, the PIL (such as hydroxyethylammonium acetate-[Eth][OAc]) is an effective solvent for biomass pretreatment and is also relatively cheap due to its ease of synthesis (Sun et al., *Green Chem.* 19(13):3152-3163 (2017)).

Deep Eutectic Solvent (DES)

DESs are systems formed from a eutectic mixture of Lewis or Brønsted acids and bases which can contain a variety of anionic and/or cationic species. DESs can form a eutectic point in a two-component phase system. DESs are formed by complexation of quaternary ammonium salts (such as, choline chloride) with hydrogen bond donors (HBD) such as amines, amides, alcohols, or carboxylic acids. The interaction of the HBD with the quaternary salt reduces the anion-cation electrostatic force, thus decreasing the melting point of the mixture. DESs share many features of conventional ionic liquid (IL), and promising applications would be in biomass processing, electrochemistry, and the like. In some embodiments, the DES is any combination of Lewis or Brønsted acid and base. In some embodiments, the Lewis or Brønsted acid and base combination used is distillable.

In some embodiments, DES is prepared using an alcohol (such as glycerol or ethylene glycol), amines (such as urea), and an acid (such as oxalic acid or lactic acid). The present invention can use renewable DESs with lignin-derived phenols as HBDs. Both phenolic monomers and phenol mixture readily form DES upon heating at 100° C. with specific molar ratio with choline chloride. This class of DES does not require a multistep synthesis. The DES is synthesized from lignin which is a renewable source.

Both monomeric phenols and phenol mixture can be used to prepare DES. DES is capable of dissolving biomass or lignin, and can be utilized in biomass pretreatment and other applications. Using DES produced from biomass could lower the cost of biomass processing and enable greener routes for a variety of industrially relevant processes.

The DES, or mixture thereof, is bio-compatible: meaning the DES, or mixture thereof, does not reduce or does not significantly reduce the enzymatic activity of the enzyme, and/or is not toxic, and/or does not reduce or significantly reduce, the growth of the microbe. A "significant" reduction is a reduction to 70, 80, 90, or 95% or less of the enzyme's enzymatic activity and/or the microbe's growth (or doubling time), if the DES, or mixture thereof, was not present.

In some embodiments, the DES, or mixture thereof, comprises a quaternary ammonium salt and/or glycerol. In some embodiments, the DES, or mixture thereof, comprises a quaternary ammonium salt and/or glycerol. In some embodiments, the quaternary ammonium salt and/or glycerol have a molar ratio of about 1:1 to about 1:3. In some embodiments, the quaternary ammonium salt and/or glycerol have a molar ratio of about 1:1.5 to about 1:2.5. In some embodiments, the quaternary ammonium salt and/or glycerol have a molar ratio of about 1:1.8 or 1:1.9 to about 1:2.1 or 1:2.2. In some embodiments, the quaternary ammonium salt and/or glycerol have a molar ratio of about 1:2. In some embodiments, the quaternary ammonium salt is a choline halide, such choline chloride.

In some embodiments, the DES is distillable if the DES can be recovered at least equal to or more than about 50%, 55%, 60%, 65%, 70%, 75%, 80%, or 85% yield by distilling over vacuum at a temperature at about 100° C., 110° C., 120° C., 130° C., 140° C., 150° C., or 160° C., or any temperature between any two of the preceding temperatures.

In some embodiments, the DES can be one taught in WO 2018/204424 (Seema Singh et al.), which is hereby incorporated in its entirety by reference.

In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the introducing step(s) produce a sugar and a lignin from the biomass. The lignin can further be processed to produce a DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the steps described herein are continuous, the one-pot composition is in a steady state.

In some embodiments, the introducing step comprises heating the mixture comprises increasing the temperature of the solution to a value within a range of about 75° C. to about 125° C. In some embodiments, the heating step comprises increasing the temperature of the solution to a value within a range of about 80° C. to about 120° C. In some embodiments, the heating step comprises increasing the temperature of the solution to a value within a range of about 90° C. to about 110° C. In some embodiments, the heating step comprises increasing the temperature of the solution to about 100° C.

Enzyme

In some embodiments, the enzyme is a cellulase. In some embodiments, the enzyme is thermophilic or hyperthermophilic. In some embodiments, the enzyme is any enzyme taught in U.S. Pat. Nos. 9,322,042; 9,376,728; 9,624,482; 9,725,749; 9,803,182; and 9,862,982; and PCT International Patent Application Nos. PCT/US2015/000320, PCT/US2016/063198, PCT/US2017/036438, PCT/US2010/032320, and PCT/US2012/036007 (all of which are incorporated in their entireties by reference).

Microbe

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/U52011/058660, PCT/U52011/059784, PCT/U52011/061900, PCT/U52012/031025, and PCT/US2013/074214 (all of which are incorporated in their entireties by reference).

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a *Rhodosporidium* species. In some embodiments, the *Rhodosporidium* species is *Rhodosporidium toruloides*.

In some embodiments the microbe is a bacterium. Bacterial host cells suitable for the invention include, but are not limited to, *Escherichia, Corynebacterium, Pseudomonas, Streptomyces,* and *Bacillus*. In some embodiments, the *Escherichia* cell is an *E. coli, E. albertii, E. fergusonii, E. hermanii, E. marmotae,* or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtherias, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum,* or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva,* or *P. plecoglossicida*. In some embodiments, the *Streptomyces* cell is a *S. coelicolor, S. lividans, S. venezuelae, S. ambofaciens, S. avermitilis, S. albus,* or *S. scabies*. In some embodiments, the *Bacillus* cell is a *B. subtilis, B. megaterium, B. licheniformis, B. anthracis, B. amyloliquefaciens,* or *B. pumilus*.

Biofuel

In some embodiments, the biofuel produced is ethanol, or any other organic molecule, described produced in a cell taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Biomass

The biomass can be obtained from one or more feedstock, such as softwood feedstock, hardwood feedstock, grass feedstock, and/or agricultural feedstock, or a mixture thereof. Softwood feedstocks include, but are not limited to, *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus semperviren*); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies,* and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, Acacia; Afzelia; *Synsepalum duloificum*; Albizia; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis/B. lutea, B.*

*pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/ Aesculus octandra*); Butternut; Catalpa; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ipe; Iroko; Ironwood (e.g. *Bangkirai, Carpinus caroliniana, Casuarina equisetifolia, Choricbangarpia subargentea, Copaifera spp., Eusideroxylon zwageri, Guajacum officinale, Guajacum sanctum, Hopea odorata, Ipe, Krugiodendronferreum, Lyonothamnus lyonii (L. floribundus), Mesua ferrea, Olea spp., Olneya tesota, Ostrya virginiana, Parrotia persica, Tabebuia serratifolia*); Jacaranda; Jotoba; Lacewood; Laurel; Limba; Lignum vitae; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoumé; Oregon Myrtle; California Bay Laurel; Pear; Poplar (e.g. *P. balsamifera, P. nigra*, Hybrid Poplar (*Populus× canadensis*)); Ramin; Red cedar; Rosewood; Sal; Sandalwood; Sassafras; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/ hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, *sorghum*, rice, soybeans, hay, potatoes, cotton, or sugarcane. The feedstock can arise from the harvesting of crops from the following practices: intercropping, mixed intercropping, row cropping, relay cropping, and the like.

In some embodiments, the biomass is an ensiled biomass. In some embodiment, the biomass is ensiled by placing the biomass in an enclosed container or room, such as a silo, or by piling it in a heap covered by an airproof layer, such as a plastic film. The biomass undergoing the ensiling, known as the silage, goes through a bacterial fermentation process resulting in production of volatile fatty acids. In some embodiment, the ensiling comprises adding ensiling agents such as sugars, lactic acid or inculants. In some embodiments, the ensiled biomass comprises one or more toxic compounds. In some embodiments, when ensiled biomass comprises one or more toxic compounds, the microbe is resistant to the one or more toxic compounds.

Example 1

Methods for "In-Situ" Ionic Liquid (IL) and Deep Eutectic Solvent (DES) Synthesis Using Chemically Synthesized or Biomass Derived Ions Materials Biomass The biomass utilized is Sorghum (*Sorghum bicolor*), which is donated by Idaho National Labs (Idaho Falls, Idaho, USA). The biomass is dried for 24 h in a 40° C. oven. Subsequently, it is a knife-milled with a 2 mm screen (Thomas-Wiley Model 4, Swedesboro, NJ). The resulting biomass is then placed in a leak-proof bag and stored in a cool dry place. Ensiled *sorghum* biomass is kindly provided by the laboratory of Daniel Putnam at the University of California, Davis and Jeff Dhalberg at Kearney agricultural research and tension center.

Chemicals

Choline hydroxide (46% in $H_2O$) and 2-aminoethan-1-ol (≥99% purity), are purchased from Sigma Aldrich (St. Louis, MO) and used as received.

Enzymes

Novozymes' (Bagsværd, Denmark) cellulase and hemicellulase complexes CELLIC® CTEC3 cellulase and HTEC3 hemicellulase are used as received.

In-Situ IL Synthesis

Methods

Biomass Pretreatment—Conventional

The biomass pretreatment is carried out using the conventional method that involves early separation (or washing) to remove the solvent after pretreatment (prior to downstream conversion). In a typical experiment, 1 g of the biomass is combined with the ionic liquid in an ace pressure tube (50 mL, Ace Glass Inc., Vineland, NJ) and homogenized. The solid loading is controlled at 15% and heated in an oil bath set to 140° C. for 3 h. After pretreatment, the mixture could cool for 30 mins and then washed 5× with deionized water using a 40 mL centrifugation-decanting cycle. The recovered solid is gravimetrically tracked to determine the solid recovery, while also passing through enzymatic hydrolysis (see below).

Biomass Pretreatment—In Situ PIL Synthesis

The biomass pretreatment is carried out using the "in-situ" method that involves the synthesis of the ionic liquid within the pretreatment vessel. In a typical experiment, 1 g of the biomass is combined with the reagents for IL synthesis in an ace pressure tube and homogenized. The reagents are loaded at the previously determined molar ratio that is necessary for IL synthesis. Next, the solid loading is controlled at 15% and the IL is synthesized in-situ while mixing. The mixture is then heated in an oil bath set to 140° C. for 3 h. After pretreatment, the mixture could cool for 30 mins and then washed 5× with deionized water using a 40 mL centrifugation-decanting cycle. The recovered solid is gravimetrically tracked to determine the solid recovery, while also passing through enzymatic hydrolysis.

Enzymatic Hydrolysis

For enzymatic hydrolysis, the 0.15 g of the pretreated biomass is loaded into a test-tube at 1.5 wt % solids loading. The liquid fraction contained 50 vol % of a 0.1 M citrate buffer (pH 5), 1 vol % $NaN_3$ and 20 mg protein/g biomass using a 9/1 mixture of the CELLIC® CTEC3 cellulase/HTEC3 hemicellulase and completed with deionized water to attain the desired solid loading. The mixture is subsequently incubated at 50° C. for 72 h in a rotary incubator (Enviro-Genie, Scientific Industries, Inc., Bohemia, NY). The amount of sugars released are quantified using HPLC after the incubation is complete.

Results and Discussion

Figure 1:
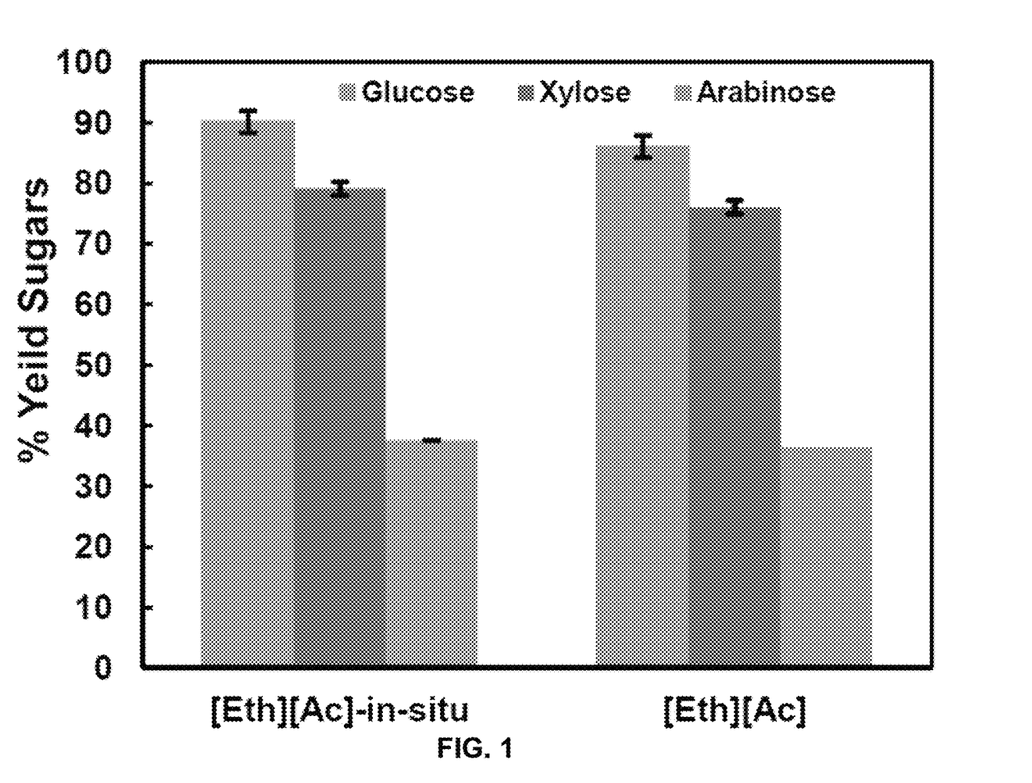
FIG. 1. Glucose and xylose yield from enzymatic hydrolysis of ethanolamine acetate pretreated samples.
Figure 2:
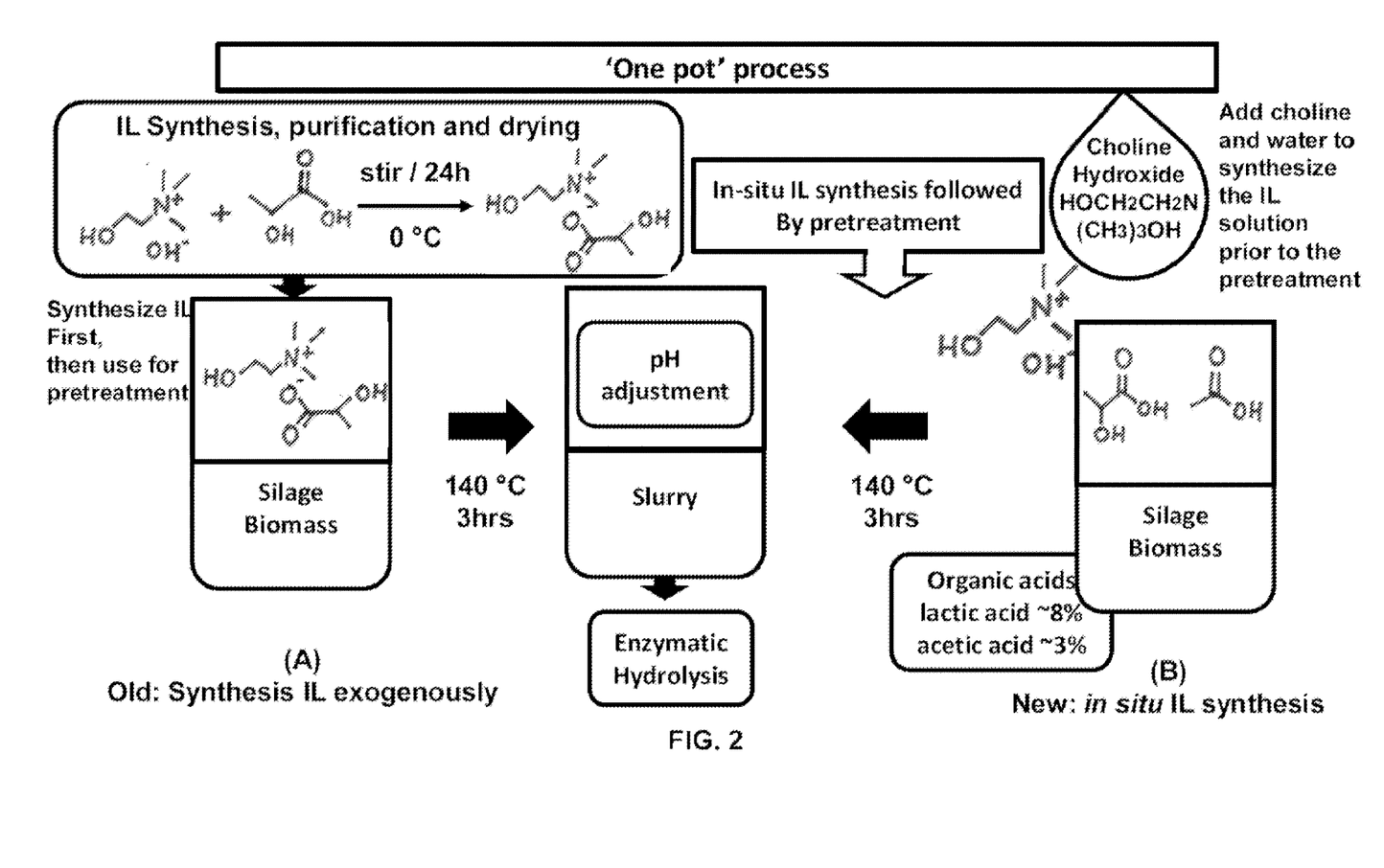
FIG. 2. One pot IL pretreatment process of ensiled *sorghum* biomass. (A) Conventional process. (B) In-situ IL synthesis followed by one pot pretreatment of ensiled *sorghum* biomass.

ILs are typically synthesized prior to use for biomass pretreatment. However, it is shown that this step can be skipped and combined with biomass pretreatment. The IL/DES components are simply added directly to the biomass in the pretreatment reactor, and pretreatment is run as normal. For example, the IL ethanolamine acetate ([Eth][OAc]) can be synthesized by adding ethanolamine and acetic acid in a 1:1 molar ratio directly to the biomass in a pretreatment reactor. The resulting biomass (post pretreatment) is just as easily hydrolyzed (into fermentable sugars) as when using pre-synthesized ethanolamine acetate (FIG. 1), thereby demonstrating the pretreatment effectiveness do not changed. [Eth][OAc] treated biomass releases ~330 mg/g biomass of sugars during enzymatic hydrolyses which is analogous to ~90% glucose and 79% xylose yields). The results show that these sugar yields do not change significantly when the IL is synthesized in-situ or exogenous to the reactor.

In-Situ IL Synthesis—Ensiled *Sorghum* Biomass One-Pot Pretreatment Methods

In-Situ IL Synthesis

The total amount of organic acids present in the ensiled biomass is calculated based on the previously reported composition analysis procedures. Cholinium hydroxide solution is added to the biomass according to the stoichiometric molar ratio of 1:1 of total organic acids. Then the mixture is continuously stirred for at least 30 min at room temperature prior to the pretreatment reaction. The addition of choline hydroxide will undergo a neutralization reaction with organic acid.

One-Pot In-Situ Ionic Liquid Pretreatment

Ensiled *sorghum* biomass (20% (w/w) initial pretreatment slurry) is mixed with [Ch][OH] loading of 3.75% ((w/w) initial pretreatment slurry) in 1 L 4520 Parr benchtop reactor (Parr Instrument Company, Moline, IL) equipped with three arms and a self-centering anchor with PTFE wiper blades. Then the one pot pretreatment reaction is carried out at 140° C. for 3 h. The same experimental conditions are used for dry *sorghum* biomass as a control.

pH Adjustment After IL Pretreatment

Although pretreating biomass with a (2.5-10) % (w/w) [Ch][Lys] concentrations resulted in higher pH values after the pretreatments and the pH values lies in the range of 8-10. Here it is observed that the use of ensiled *sorghum* in-situ pretreatment results in pH values (pH=5.40) that are closer to the optimum values required for saccharification for higher sugar yields. Since the pH is very closer to the optimal range this can potentially be saccharified without performing a pH adjustment.

Enzymatic Hydrolysis

Commercial enzyme cocktails containing cellulase CELLIC® CTEC3 cellulase) and hemicellulase CELLIC® HTEC3 hemicellulase) mixed at a 9:1 (v/v) ratio are then directly added at an enzyme loading of 10 mg enzyme product per one gram of starting biomass. Three glass beads are added to each vial to facilitate mixing during enzymatic hydrolysis. Enzymatic hydrolysis is conducted at 50° C. for 72 h with constant agitation on an Enviro Genie SI-1200 rotator platform (Scientific Industries, Inc., Bohemia, NY).

Results and Discussion

Current pretreatment methods based on severe physiochemical processes are effective, but they can be costly and energy intensive. Alternatively, many Ionic liquids (ILs) have been shown to be effective at biomass pretreatment and require less severe pretreatment conditions to reduce the recalcitrance of lignocellulose to enzymatic hydrolysis. For example, cholinium lysinate [Ch][Lys] in 90% water, has been demonstrated to be effective for biomass pretreatment in a one-pot configuration owing to its effectiveness in solubilizing lignin. However, ILs contribute to the overall cost of a lignocellulosic conversion process, so methods to reduce their costs can have a big impact on the overall economics of a biorefinery.

Therefore, this invention features a way to synthesize the IL in-situ (during pretreatment) through a novel approach of using ensiled biomass (wet biomass). Ensiled biomass normally contains organic acids such as lactic acid and acetic acid around ~10% (w/w). In this approach these organic acids are utilized and incorporated into ionic liquid materials in the form of organic anions. The direct addition of [Ch][OH] solution into the ensiled biomass resulted in the ionic liquid formation inside the pretreatment vessel. Then the pretreatment is performed using a one-pot conversion process at 140° C., 3 h reaction time for 20% (w/w) biomass loading.

Figure 3:
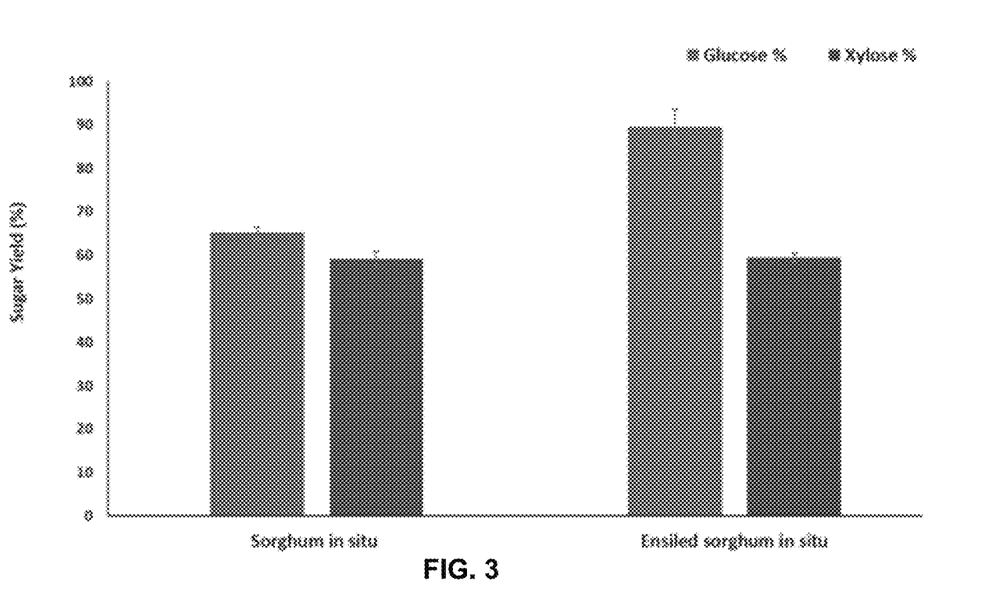
FIG. 3. Sugar yields from the in-situ IL pretreated ensiled *sorghum* and dry *sorghum* biomass (expressed as the percentage of the theoretical maximum based on the initial glucan and xylan contents in the starting biomass).

The biomass deconstruction efficiency of in-situ IL pretreatment is evaluated through the sugar conversions after enzymatic hydrolysis via HPLC spectroscopy. As expected, in-situ pretreatment of ensiled biomass released almost ~90% glucose and ~60% of xylose yields, while dry *sorghum* resulted in ~65% glucose and ~55% xylose yields. (FIG. 3) This confirmed that the organic acids in the ensiled biomass contributed towards the IL formation as anions upon addition of [Ch][OH] solution. Also, the resulted higher sugar yields strongly suggest that the organic acids/anions presence in the ensiled *sorghum* biomass do not have any negative effect on the enzymatic activity during the saccharification process. Somehow the organic acid content in dry *sorghum* biomass is negligible. As the controlled pretreatment experiment, only the starting material ([Ch][OH]) involved in the dry *sorghum* biomass pretreatment and therefore it resulted in comparatively low sugar yields due to the incomplete biomass deconstruction.

Figure 4:
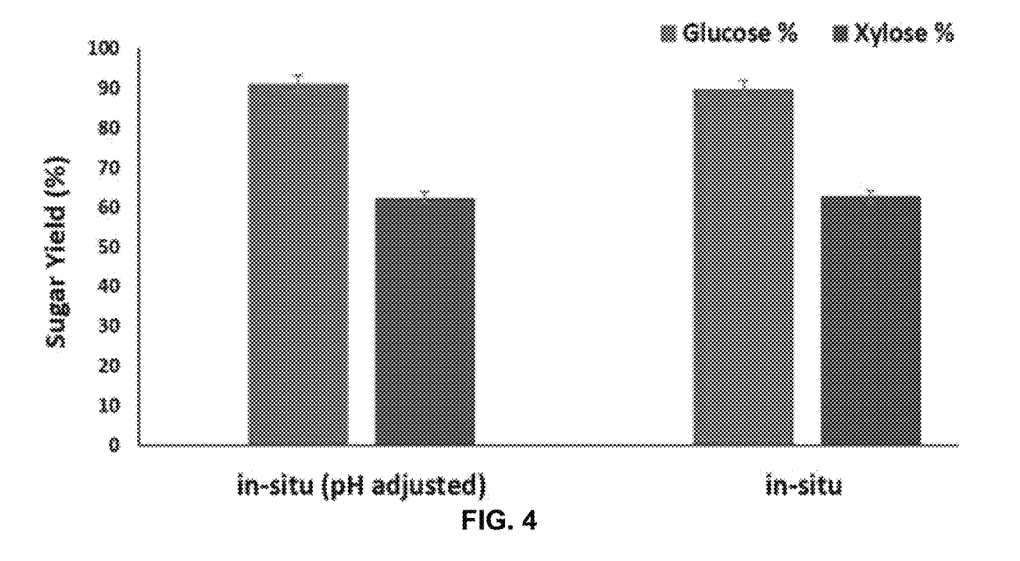
FIG. 4. Sugar yields from the in-situ IL pretreated and in-situ pretreated with pH adjusted ensiled *sorghum* biomass (expressed as the percentage of the theoretical maximum based on the initial glucan and xylan contents in the starting biomass).

As previously mentioned, the saccharification of in-situ IL pretreated ensiled *sorghum* biomass resulted in almost ~90% glucose and ~60% of xylose yields. Interestingly here, fluctuations of the sugar yields are not observed even without a pH adjustment which normally requires after the pretreatment. (FIG. 4). This could be another important advantage of "one pot in-situ ensiled biomass pretreatment" to reduce capital and operating costs at large scale biofuel production.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to deconstruct a biomass: the method comprising:
   (a) ensiling a biomass to produce an ensiled biomass comprising equal to or more than 10% by weight of one or more organic acids;
   (b) introducing one or more components of an ionic liquid (IL) or deep eutectic solvent (DES) to the ensiled biomass, wherein the one or more components, and one or more organic acids already present in the ensiled biomass, form an ionic liquid (IL) or deep eutectic solvent (DES), or mixture thereof, which solubilizes the ensiled biomass to form a solubilized biomass mixture, and wherein the ensiled biomass has a solid loading of about 15% to about 40%, and the one or more components comprises an ethanolamine; and
   (c) introducing an enzyme and/or a microbe to the solubilized biomass mixture such that the enzyme and/or microbe produces a sugar from the solubilized biomass mixture; wherein the ensiled biomass is an ensiled lignocellulosic biomass.

2. The method of claim 1, wherein the one or more components that form the IL comprise cations and anions.

3. The method of claim 2, wherein the introducing step (a) comprises introducing two or more components to the ensiled biomass, wherein the two or more components form an IL, or mixture thereof.

4. The method of claim 1, wherein the one or more components introduced that form the DES are selected from the group consisting of halide salts, organic salts, organic acids, and amines.

5. The method of claim 4, wherein the introducing step (b) comprises introducing two or more components to the ensiled biomass, wherein the two or components form a DES, or mixture thereof.

6. The method of claim 1, wherein the introducing step (b) comprises introducing each component separately to the ensiled biomass.

7. The method of claim 1, wherein the one or more organic acids comprises an alkanoic acid.

8. The method of claim 7, wherein the alkanoic acid is lactic acid or acetic acid.

9. The method of claim 1, wherein one or more individual components comprises choline hydroxide or choline chloride.

10. The method of claim 1, further comprising: separating the sugar from the solubilized biomass mixture.

11. The method of claim 2, wherein the cation is an amine containing molecule, and the anion is a mineral or an organic acid.

12. The method of claim 11, wherein the amine containing molecule is choline, and anion is sulfuric acid or acetic acid.

13. The method of claim 4, wherein the one or more individual components that form the DES are selected from the group consisting of choline chloride, zinc chloride, ammonium acetate, acetic acid, lactic acid, tartaric acid, ethylene glycol, propanediol, glycerol, glucose, urea, acetamine, and thiourea.

14. The method of claim 1, wherein the biomass is obtained from a softwood feedstock, hardwood feedstock, grass feedstock, agricultural feedstock, or a mixture thereof.

15. The method of claim 1, wherein the ensiled biomass has a solid loading of about 20% to about 40%.

16. The method of claim 1, wherein the introducing step (c) results in a yield of equal to or more than about 80% of sugar from the ensiled biomass.

17. The method of claim 16, wherein the introducing step (c) results in a yield of equal to or more than about 90% of sugar from the ensiled biomass.

* * * * *